_(12)_ United States Patent
Jensen et al.

(10) Patent No.: US 6,181,960 B1
(45) Date of Patent: Jan. 30, 2001

(54) BIOPSY MARKER DEVICE

(75) Inventors: Mary Elizabeth Jensen, Crozet, VA (US); Laurie L. Fajardo, Ellicott City, MD (US)

(73) Assignee: University of Virginia Patent Foundation

( * ) Notice: Under 35 U.S.C. 154(b), the term of this patent shall be extended for 0 days.

(21) Appl. No.: 09/232,873

(22) Filed: Jan. 15, 1999

Related U.S. Application Data

(60) Provisional application No. 60/071,378, filed on Jan. 15, 1998.

(51) Int. Cl.⁷ .................................................. A61B 17/00
(52) U.S. Cl. ............................................ 600/431; 606/116
(58) Field of Search ..................................... 600/407, 431, 600/434; 604/164, 264, 93; 606/116, 130, 185, 117

(56) References Cited

U.S. PATENT DOCUMENTS

| | | | |
|---|---|---|---|
| 4,345,606 | 8/1982 | Littleford | 128/784 |
| 4,592,356 | 6/1986 | Gutierrez | 128/339 |
| 4,774,948 | 10/1988 | Markham | 128/329 R |
| 4,790,329 | 12/1988 | Simon | 128/749 |
| 5,059,197 | 10/1991 | Urie | 606/116 |
| 5,127,916 | 7/1992 | Spencer | 606/185 |
| 5,158,565 | 10/1992 | Marcadis | 606/185 |
| 5,665,092 | 9/1997 | Mangiardi | 606/86 |
| 5,800,445 | 9/1998 | Ratcliff | 606/116 |
| 5,853,366 | 12/1998 | Dowlatshahi | 600/434 |

*Primary Examiner*—Marvin M. Lateef
*Assistant Examiner*—Eleni Mantis Mercader
(74) *Attorney, Agent, or Firm*—Robert J. Decker

(57) ABSTRACT

A radiographic marker is disclosed to indicate a biopsy site and entry path. The marker has an arrow shape configuration with a shaft and a pair of limbs extending from the shaft at an angle of less than about 90°. The tip of the arrow indicates the biopsy site and the shaft indicates the said entry path. The marker preferable is a single piece of wire, having a diameter of less than 0.010 inches, folded to four sections, to form the limbs and shaft of the arrow. Fibers can be affixed to the shaft to cause the marker to fibrose within the tissue. An introducing device, having a body and a hub, is used to insert the marker. The introducing device body has an interior diameter dimensioned to hold the shaft of the marker. A marker pusher is dimensioned to fit within the introducing device and is used to deploy the marker into the tissue. A cannula, dimensioned to receive the body and hub of the introducing device, has a pair of receiving channels within the interior of the body to receive the limbs of the marker.

2 Claims, 5 Drawing Sheets

BIOPSY MARKER DEVICE

This is a continuation-in-part of copending application Ser. No. 60/071,378 filed on Jan. 15, 1998.

BACKGROUND OF THE INVENTION

1. Field of the Invention

The invention relates to a non-migrating, directional radiographic marker for an indicating the position and entry direction of a biopsy site.

2. Brief Description of the Prior Art

In many cases it is necessary for a surgeon to localize a portion of tissue or foreign matter in the tissue that is to be removed in an operative procedure. The localization of tissue also occurs during biopsies wherein the location of the biopsy tissue must be reproducible in the event further biopsy or surgery is required. To facilitate the location of the tissue or foreign matter, markers are temporarily inserted into the tissue at the required location. Problems have occurred when a needle biopsy of a breast lesion is performed and the radiographic evidence of the breast lesion is either distorted or inadvertently removed. When needle biopsy pathology shows carcinoma, further localization must be accomplished to surgically excise the entire cancer. If radiographic evidence of the lesion is no long well defined or is no longer present, subsequent localization is problematic.

One prior art method is the use of a hypodermic needle placed into the breast to location the lesion. When the needle is properly placed, a stainless steel wire having a hairpin hooked-end portion is slide through the needle to engage the body tissue, thereby retaining the needle adjacent to or at the breast lesion. The hypodermic needle is withdrawn over the wire and the wire anchored until after surgery. However, the compression of the breast during mammographic filming and situation of the needle can cause the needle to move or be displaced with respect to the breast lesion. U.S. Pat. No. 4,592,356 discloses the use of a localization device having a needle with an anchoring device at a distal end to firmly anchor the needle into the tissue. A clamping device is provided at the proximal end to anchor the needle to the skin. The rigid needle keeps the barbs and needle in place until removal.

U.S. Pat. No. 5,127,916 discloses a localization needle that is readily positioned and locked within body tissue to locate pinpoint lesions. The '916 device utilizes a barb to lodge the marker within the tissue. In U.S. Pat. No. 5,158,565 a hollow needle hub is used to anchor the proximal end of a barbed stylet and releasably retains the surrounding needle for movement from a sheathing position for the barb to a position projecting the barb outside the needle. The hub is a one-piece split body resiliently closed and expanded by a surgeon's action to release the cannula or hollow needle for sliding movement to retract or expose the barb.

U.S. Pat. No. 5,853,366 discloses a two and three legged V-shaped resilient member that is capable of being positioned wholly within the body of a patient. The resiliency of the legs of the V-shape enables the marker to collapse to a reduced size while be inserted along the hollow dispenser, resuming its original V-shape upon discharge from the guide member. Neither of the embodiments, however, provide any method of anchoring the device within the tissue. Further, as the third leg is design approximately parallel with the other two legs, there is nothing to prevent the device from flattening or rotating. Once the legs, whether there are two or three, flatten, the marking device becomes a linear bar, rendering it impossible to know where it was pointing upon its initial positioning.

A Lesion Location Device is described in U.S. Pat. No. 5,059,197 that uses a wire bent at a 180 degree angle, forming a first and second portion. A third portion extends adjacent the second portion and continues beyond the bend in a direction substantially opposed to the second portion. The pivotable bend forms a spring mechanism to prevent ingress of the wire once placed.

U.S. Pat. No. 5,800,445 discloses a Tissue Tagging Device for marking the location of lesions. This marking device, in its main embodiment, utilizes a wire marker that is inserted through an elongated tube. Another embodiment includes an arcuate anchor in addition to the wire marker.

As can be seen, prior art marking devices include straight, curved or helical coil markers, however these do not necessarily point to the exact approach taken to obtain the biopsy. Check-mark shaped indicators and act like porcupine quills and ratchet through the tissue with movement, thus being susceptible to migration within the tissue. V-shaped coils can flatten with time and straighten or distort, thereby eliminating the exact approach area. Additionally, the hooks used in the prior art are internally "anchored" within the fatty tissue within the breast, which does not always provide sufficient anchoring and/or stability to the hook-wire combination.

The prior art devices also address predominately marking lesions for surgery, not the time span between biopsies or biopsy to surgery. Most of the prior art devices cannot be left in the patients body to serve as a marker for future procedures, but rather are removed within a short period of insertion.

The disclosed device overcomes the prior art problems by inserting a small marker device through the biopsy needle at the time of biopsy, thereby providing a radiographic target for future localization in the event of surgery.

SUMMARY OF THE INVENTION

A radiographic marker is disclosed to indicate a biopsy site and entry path. The marker has an arrow shape configuration with a shaft and a pair of limbs extending from the shaft at an angle of less than about 90°. The tip of the arrow indicates the biopsy site and the shaft indicates the said entry path. In the preferred embodiment the marker is a single piece of wire folded to four sections, the first and fourth sections forming the limbs and a second and third sections lying adjacent one another and forming the shaft. The second and third sections are affixed to one another, through soldering or other methods, to form the shaft. Preferably the wire has a diameter of less than 0.010 inches. Fibers can be affixed to the shaft prior to affixing the second and third sections. The fibers cause the marker to fibrose within the tissue surrounding the biopsy site to ensure that the marker remains immobile within the tissue. The shaft has a diameter greater than the diameter of the limbs and is usually about twice the diameter of the limbs. A center support can be affixed to the shaft to provide additional rigidity.

An introducing device, having a body and a hub, is used to insert the marker. The introducing device has a diameter greater than the body and is connected to the body by an angled wall. The introducing device body has an interior diameter dimensioned to hold the shaft of the marker. The introducing device also has an end stop extending at right angles from the hub. In some embodiments a stop flange, having a diameter less than the shaft, can be placed within the interior to prevent the marker from being inserted beyond the stop flange.

A marker pusher, having a first end, a second end and a shaft, is dimensioned to fit within a deployment device and is used to deploy the marker into the tissue. The marker pusher preferably has an indicator line to indicate the distance to insert the marker pusher into the deployment device. The deployment device can be an introducing device or a biopsy needle.

A cannula, dimensioned to receive the body and hub of the introducing device, has a a pair of receiving channels within the interior of the body. The receiving channels are dimensioned to receive the limbs of the marker.

BRIEF DESCRIPTION OF THE DRAWINGS

The advantages of the instant disclosure will become more apparent when read with the specification and the drawings, wherein.

DETAILED DESCRIPTION OF THE INVENTION

After a core biopsy is performed it is optimal to both patient and physician to have the ability to relocate the specific site of the biopsy. Various problems are incurred with the prior art marking devices, such as inadequately designing the exact approach used for the biopsy or, depending upon biopsy location, moving within the soft fatty tissue. The arrow also forms a head that points to the site and, by positioning the head to the location of the site, the shaft naturally indicates the path of entry. The limbs of the arrow prevent movement within the tissue, thereby prevent the entry path from being obscured. Nor will the arrow flatten with time as encountered with a simple V-shaped coil. Although the following disclosure makes reference to breast biopsies, it should be noted that the arrow can be used to indicate the location, and entry direction, of any lesion.

Figure 1:
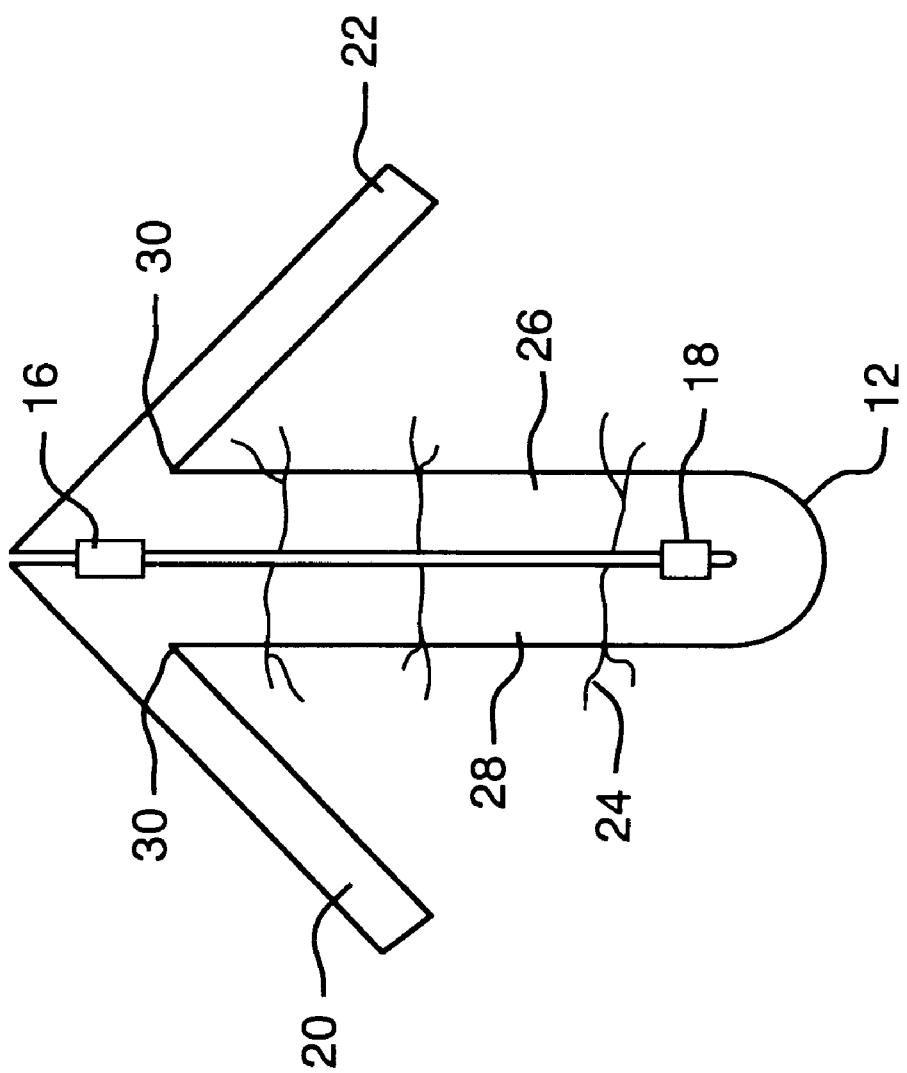
FIG. 1 is a front view of the disclosed arrow shaped biopsy marker.
Figure 6:
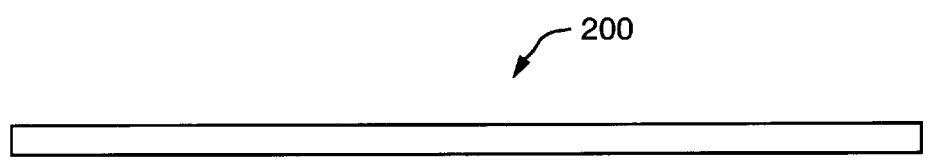
FIG. 6 is a top view of a wire for use with the disclosed marker.
Figure 7:
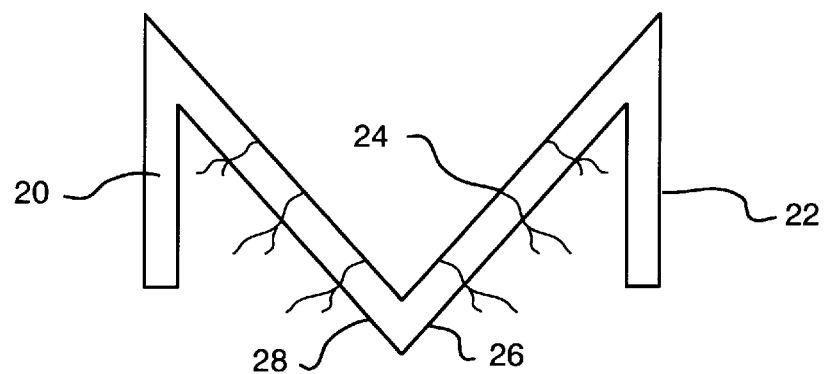
FIG. 7 is a side view of the wire of FIG. 6 bent in the for affixing the fibers.

The arrow-shaped marker 10, illustrated in FIG. 1, is constructed with stainless steel, platinum, nitinol, titanium, or other medically acceptable inert material. It should be noted that depending upon the placement of the marker and the imaging method, the inert material can require impregnation with a radiopaque substance. The impregnation of an inert material, such as plastics, will become evident to those skilled in the medical imaging arts. The arrow-shaped marker 10 consists of a shaft 12 and two limbs 20 and 22 that are constructed from a single strand of finely ground wire having a diameter of less than 0.010 inch. The configuration is such that the shaft 12 has a diameter approximately double the diameter of the limbs 20 and 22. As the marker 10 is, in its easier manner of construction, made from a single piece of wire the shaft 12 is inherently double the limbs 20 and 22. If other means of construction are used, such as molding, the shaft diameter can vary. The formation of the marker 10 using a single wire is illustrated in FIGS. 6 and 7. The wire normally has a diameter of less than 0.010 inch, however, this can vary dependent upon final application and the appropriate diameter use for a particular application will be apparent to those skilled in the medical arts. As shown in FIG. 7, the wire is bent into a modified "M" shape forming the limbs 20 and 22 and the shaft wires 26 and 28. While in this configuration the fibers 24, if used, are tied to the shaft wires 26 and 28. Once the fibers 24 have been added, the shaft wires 26 and 28 are bent further, placing them adjacent one another, to form the arrow shaped marker 10. To maintain the shaft wires 206 and 208 adjacent one another to form a single shaft 12, the shaft wires 26 and 28 are spot soldered at upper solder 16 and lower solder 18. Although two solder locations are illustrated herein, the shaft wires 26 and 28 can be soldered in additional locations or along the entire length. The number of soldering locations must take into consideration the number of fibers 24, if any, tied to the shaft wires 26 and 28 and length of the shaft.

Figure 8:
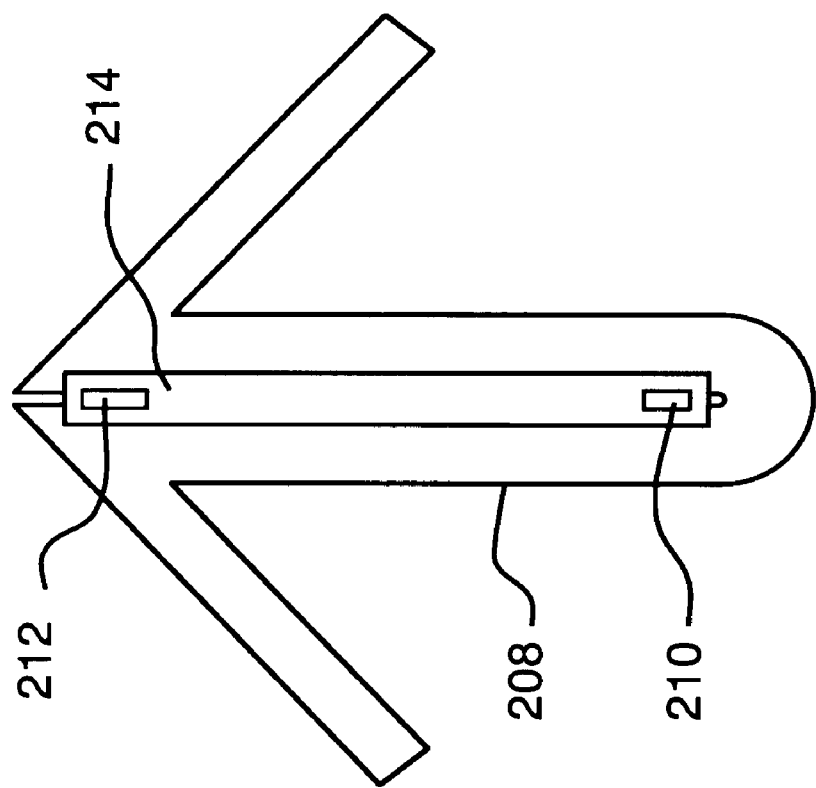
FIG. 8 is a front view of an alternate embodiment of the disclosed marker.

In the event the additional structural support is required, a center support 214 can be included, as illustrated in FIG. 8 in conjunction with arrow marker 208. The center support 214 is spot welded at approximately the top and bottom of the support 214 at welding points 212 and 210. Although not always required, the center support 214 does provide the additional rigidity required in some situations.

The limbs 20 and 22 create approximately a 90 degree angle to one another, although this exact angle is not critical. A 180 degree angle creates a "T" shape which, although the shaft will remain pointing at the site, does reduce slightly the visual benefits of the arrow.

The strands of fiber 24, such as dacron, are tied to the shaft 12 to ensure that the shaft 12 will fibrose within the tissue, adding additional assurance that the marker 10 will not migrate. If fibrosis is undesirable, the fibers can be eliminated. Although other fibers known to cause fibrosis can be used, such as silk, the level of resulting inflammation must be considered and the material chosen accordingly. In the illustrated embodiment, six (6) strands 24 of dacron are used, three (3) strands on each side, however, this is for illustration purposes only and the number of strands used can be increased or decreased dependent upon individual factors, such as marking location, patient tolerance to inflammation and/or length of shaft.

Figure 2:
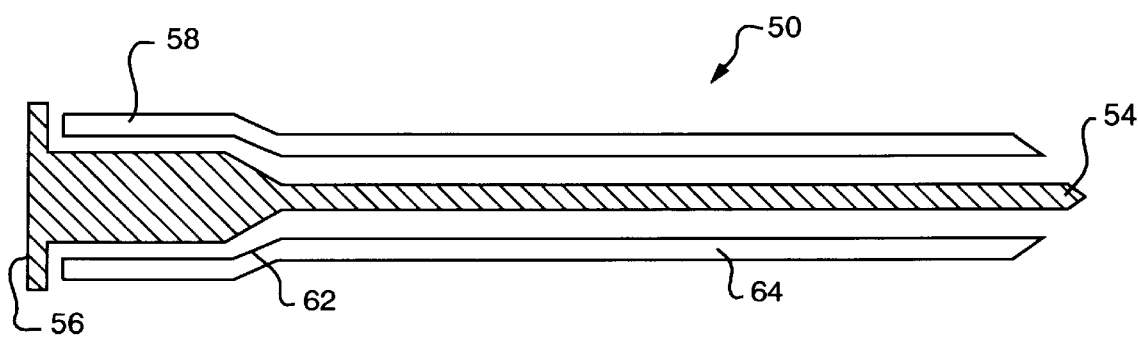
FIG. 2 is a cutaway side view of the localization device used.
Figure 3:
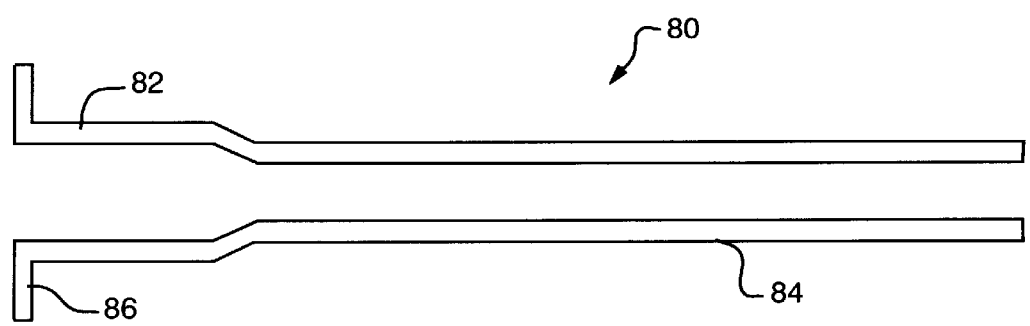
FIG. 3 is a cutaway side view of the marker introduction device.

The localization device 50 consists of a thin walled, stainless steel beveled outer cannula 52 and an inner 14 gauge diamond-point stylet 54 with an interlocking hub 56, as illustrated in FIG. 2. Although reference is made herein to the use of a cannula, it should be noted that other devices, such as a biopsy needle, that meet the criteria set forth herein can be used. The hub legs 60 and 62 are angled at an angle equal to the angle of the limbs 20 and 22 of the marker 10. The localization device 50 makes the initial entry to the point of lesion, guided through either stereotaxic x-ray or sonographic imaging guidance. After removing the inner stylet 54, a thin-walled 16 gauge marker introducer 80 is slid into the outer cannula 52. The introducer 80 has a hub 82 with an outer diameter slightly less than the inner diameter of the cannula hub 58, enabling the introducer hub 82 to reproducibly seat within the cannula hub 58. The marker 10 is mounted into the end of the introducer 60 and advanced into, and along, the outer cannula 52 until the hub 62 Sits firmly within the cannula hub 58. The length of the body 84 of the introducer 80 is equal to, or slightly greater than, the length of the cannula body 64, thereby placing the marker 10 outside the cannula body 64 and within the tissue, when the introducer 80 is fully seated within the cannula 52. An end stop 86 preferably extends around the periphery of the hub 82. The end stop 86 serves to provide a secondary preventative to prevent the introducer 80 from entering too far into the cannula 52. The end stop 86 also provides a gripping surface to enable easier insertion.

Figure 4:
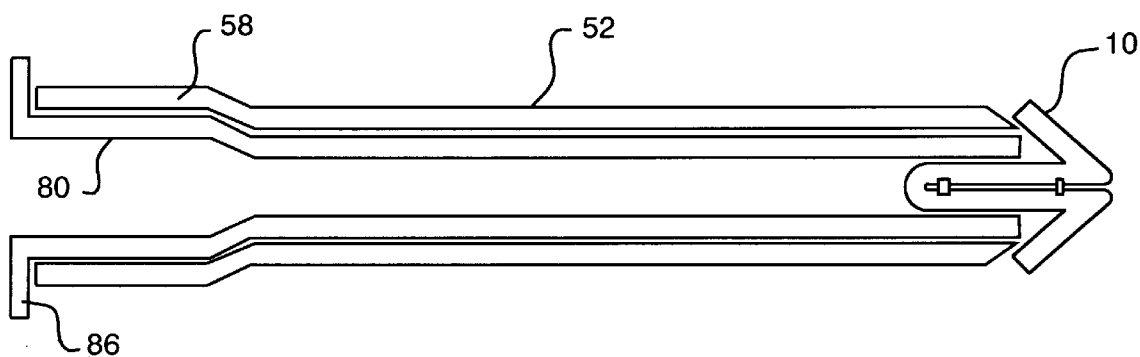
FIG. 4 is a cutaway side view of the marker introduction device inserted into the outer portion of the localization device.
Figure 5:
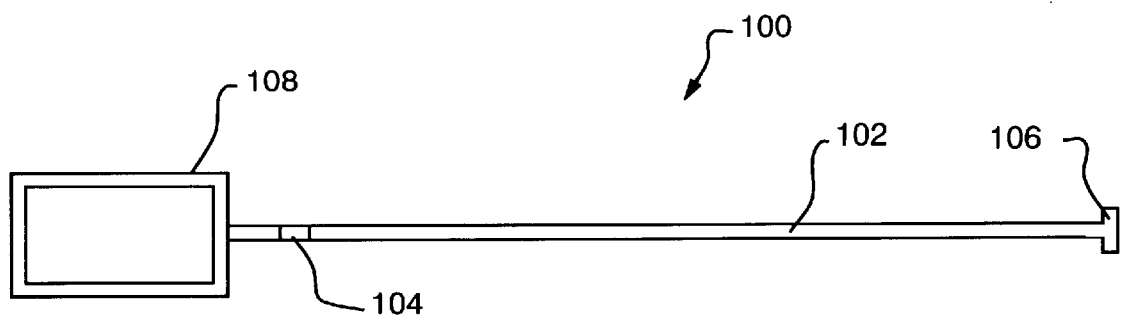
FIG. 5 is a side view of the marker insertion device.

The marker 10 is maintained within the tip of the introducer 80 through a slight friction fit. As the marker 10 needs to be easily removed from the introducer 80, any friction between the two elements must be minimal. The limbs 20 and 22 of the marker 10 are designed to flex, fitting within the cannula body 64. The sloped sides 60 and 62 of the hub 58 of the localization cannula 52 have the same angles as the limbs 20 and 22 on the marker 10 to allow ease of introduction. Once the marker 10 reaches the end of the cannula body 64 the limbs 20 and 22 open within the tissue. The marker 10 is then deployed into position within the tissue through the use of a marker pusher 100 as illustrated in FIG. 5. The pusher 100 consists of a head 108, shaft 102 and marker contact 106. The head 108 is dimensioned to fit within the introducer hub 82 with insertion depth being controlled by the dimensioning between the two elements. The shaft 102 has a length sufficient to place the marker contact 106 proximate the open end of the introducer 80 when fully inserted with the head 108 seated within the hub 82. The marker contact 106 has a diameter proximate the interior diameter of the introducer 80 to provide maximum contact with the marker shaft 12 and enable maximum accuracy during deployment. The final deployment of the marker 10 within the tissue can be accomplished using several methods. In one method, the marker pusher 100 is inserted into the introducer 80, as described above, and the marker 10 positioned in the tissue. Alternatively, the marker 10 can initially be deployed into the tissue, as illustrated in FIG. 4, and the introducer 80 withdrawn from the cannula 52. The marker pusher 100 is then inserted directly into the cannula 52, placed against the back end of the marker 10, and the marker 10 deployed into position within the tissue. The head 108 of the pusher 100 is dimensioned to interact with the hub 82 of the introducer 80 to provide a reproducible deployment distance. When the pusher 100 is inserted into the cannula 52, this interaction does not take place. To provide a reproducible deployment distance, an indicator band 104 marks where the pusher 100 should align with the back end of the cannula 52 for deployment.

The ability to repeatedly place the marker 10 a known distance from the end of the cannula or introducer is a distinct advantage to the disclosed device. The interaction between the hubs, the stop end and the marking line provides a reproducible known distance critical to accurate placement of the marker.

Figure 9:
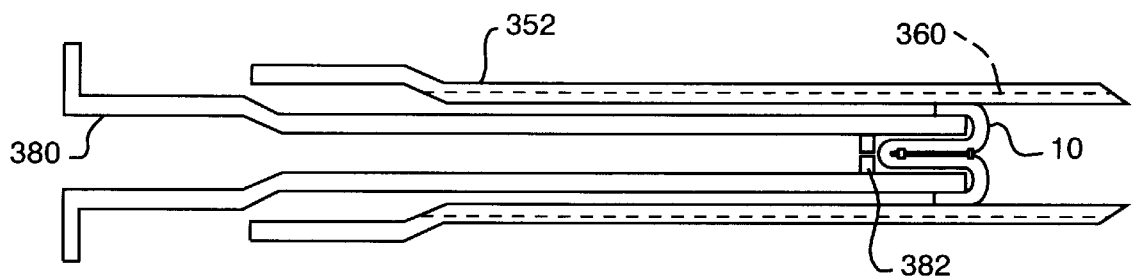
FIG. 9 is a cutaway side view of an alternate cannula and introducer for use with the disclosed biopsy marker.
Figure 10:
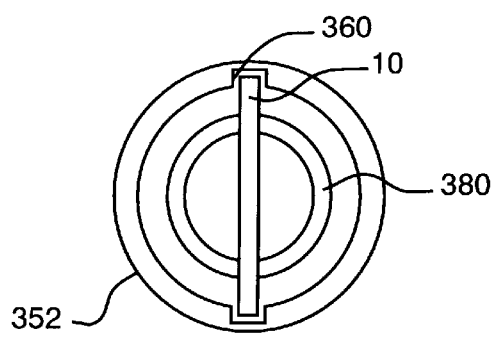
FIG. 10 is an end view of the cannula and introducer of FIG. 9.

In FIGS. 9 and 10 an alternate embodiment is illustrated with the cannula 352 having a receiving groove 360 to receive the marker 10. The receiving groove 360 enables the user to insert the marker 10 without requiring as much flex in the limbs 20 and 22, as well as preventing the marker 10 from twisting or angling within the cannula 352. The introducer 380 of FIG. 9 includes a stop flange 382 that prevents the user from inserting the marker 10 further than the predetermine distance. Thus, the marker 10 will be reproducibly inserted the appropriate distance to enable the limbs 20 and 22 to wrap around the outside of the introducer 380. The end of the introducer 380 is thus prevented from either straightening the limbs 20 and 22 or forcing the limbs 20 and 22 to bend at an area other than the apex 30.

In an alternate method, the thin walled 16 gauge introducer 80 can be introduced through the hub of the outer cannula of a traditional 14 gauge core biopsy needle and deployed in a similar fashion.

What is claimed is:

1. A method of making a radiographic biopsy marker using a wire comprising the steps of:

cutting said wire to a predetermined length, dividing said wire into four sections, a first and fourth section having about an equal length and said second and third section having about an equal length, said second and third section length being greater than said first and fourth section length, folding said wire into four sections to form an "M" shape, closing said "M" to place said second and third sections adjacent one another, affixing said second and third sections together to form a shaft, wherein said first and fourth sections form limbs to an arrow and said second and third sections form a shaft, said arrow providing a marker to indicate location of, and entry path to, a biopsy site.

2. The method of claim 1 further comprising the step of affixing fiber to said second and third section prior to closing said "M" shape, said fibers causing surrounding tissue to fibrose around said marker to secure said marker's location within said tissue.

\* \* \* \* \*